(12) United States Patent
Dalla Pria

(10) Patent No.: US 7,608,109 B2
(45) Date of Patent: Oct. 27, 2009

(54) ATTACHMENT ELEMENT FOR A PROSTHESIS FOR THE ARTICULATION OF THE SHOULDER

(75) Inventor: Paolo Dalla Pria, Udine (IT)

(73) Assignee: Lima LTO SpA, Villanova Di San Daniele Del Friuli (IT)

( * ) Notice: Subject to any disclaimer, the term of this patent is extended or adjusted under 35 U.S.C. 154(b) by 12 days.

(21) Appl. No.: 11/589,806

(22) Filed: Oct. 31, 2006

(65) Prior Publication Data

US 2007/0100458 A1    May 3, 2007

(30) Foreign Application Priority Data

Nov. 3, 2005    (IT) .......................... UD2005A0185

(51) Int. Cl.
*A61F 2/40* (2006.01)
(52) U.S. Cl. ................................. 623/19.11; 623/19.13
(58) Field of Classification Search ... 623/19.11–19.14, 623/20.34, 22.35–22.36, 23.41, 22.15, 22.38
See application file for complete search history.

(56) References Cited

U.S. PATENT DOCUMENTS

| 3,803,641 | A |   | 4/1974  | Golyakhovsky |           |
|-----------|---|---|---------|--------------|-----------|
| 3,842,442 | A | * | 10/1974 | Kolbel       | 623/19.12 |
| 4,919,669 | A | * | 4/1990  | Lannelongue  | 623/19.12 |
| 5,507,819 | A |   | 4/1996  | Wolf         |           |
| 6,228,119 | B1 | * | 5/2001 | Ondrla et al.| 623/19.11 |
| 6,488,716 | B1 |   | 12/2002| Huang et al. |           |
| 2004/0024468 | A1 |   | 2/2004 | Lualdi et al. |         |
| 2004/0220673 | A1 |   | 11/2004 | Pria       |           |
| 2004/0260399 | A1 |   | 12/2004 | Chieng     |           |

FOREIGN PATENT DOCUMENTS

| DE | 24 10 057  | B1 | 7/1975  |
|----|------------|----|---------|
| EP | 1048274    |    | 11/2000 |
| EP | 1388329    |    | 2/2004  |
| EP | 1 472 999  | A1 | 4/2004  |
| EP | 1437099    |    | 7/2004  |
| EP | 1488764    |    | 12/2004 |
| EP | 1 591 084  | A1 | 11/2005 |
| FR | 2 579 454  |    | 10/1986 |
| FR | 2631539    |    | 11/1989 |
| FR | 2674122    |    | 9/1992  |
| FR | 2683142    |    | 5/1993  |
| FR | 2 704 747  |    | 11/1994 |
| FR | 2784289    |    | 4/2000  |
| FR | 2854057    |    | 10/2004 |

\* cited by examiner

*Primary Examiner*—Corrine M McDermott
*Assistant Examiner*—Megan Wolf
(74) *Attorney, Agent, or Firm*—Novak Druce + Quigg LLP

(57) ABSTRACT

Attachment element for a prosthesis of the shoulder for the articulation of a humerus in a scapula of a shoulder having a glenoid cavity. The prosthesis comprises a first articulation element associated with the top of the humerus, and a second articulation element associated with the glenoid cavity. The attachment element comprises a first part for removable anchorage to the first or second articulation element, and a second part for attachment of the prosthesis to the bone part of the scapula in a position outside the bulk of the first and second articulation element.

19 Claims, 4 Drawing Sheets

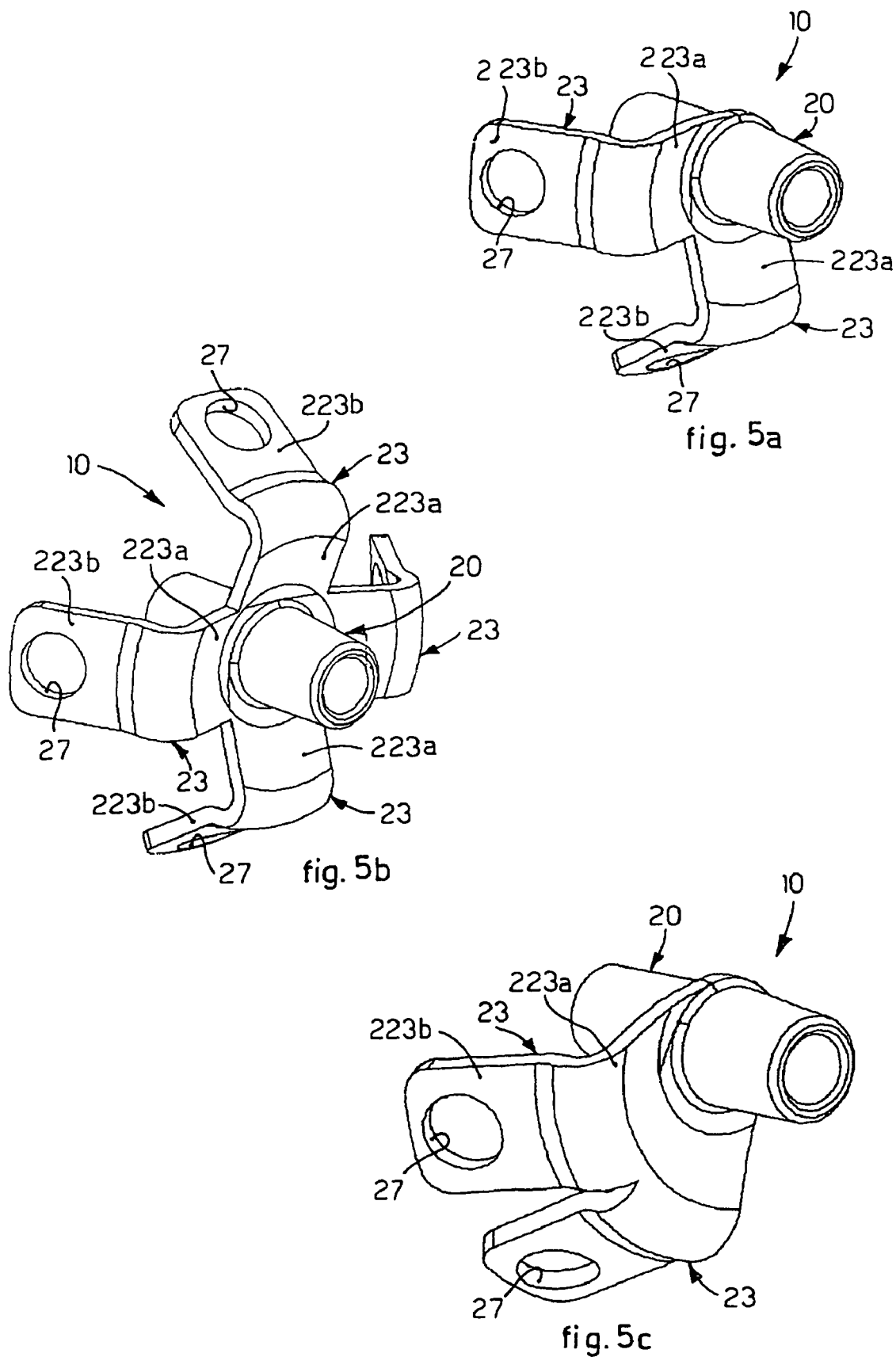

ATTACHMENT ELEMENT FOR A PROSTHESIS FOR THE ARTICULATION OF THE SHOULDER

FIELD OF THE INVENTION

The present invention concerns an attachment element which allows to attach, in a stable and secure manner, a prosthesis for the articulation of the shoulder to the glenoid cavity of the scapula.

BACKGROUND OF THE INVENTION

So-called anatomical prostheses of the shoulder are known, which reproduce naturally the gleno-humeral anatomy, and comprise a glenoid insert anchored to the scapula by means of a support attached to the glenoid cavity; the insert articulates with a spherical element attached to the top of the humerus by means of a supporting body and an attachment rod inserted into the humerus itself.

So-called inverse prostheses of the shoulder are also known, which reproduce the gleno-humeral anatomy in an inverse manner, and which, unlike anatomical prostheses, comprise a spherical element attached to the scapula and a mating humeral cup or insert attached to the upper end of the humerus.

In order to anchor the support to the glenoid cavity it is usually provided to insert into the bone seating a rod substantially passing through the axis of the support, and to use two or more screws that attach to the bone seating a platelet solid with the rod. The screws are normally disposed on the periphery of the rod, and are attached on the scapula substantially along the same direction as the rod.

Due to particular bone pathologies, or the anatomical morphology of the scapula, or the lack of a sufficient bone thickness, known attachment solutions are not always able to guarantee a correct and enduring attachment of the support to the glenoid cavity. This may entail possible mechanical yielding of the prosthetic part constrained to the glenoid cavity, and consequent problems, obviously, for the patient concerning the progressive loosening and possible reciprocal detachment of the components of the prostheses.

Moreover, even in substantially normal bone conditions, it may be difficult for the surgeon, given the extremely limited space available, to intervene with medical instruments in order to screw the traditional screws inside the bone of the scapula, and this may cause a non-optimum attachment of the support.

EP-A1-1.488.764, in the name of the Applicant, discloses an inverse prosthesis able to be disassembled and comprising a double-conical pin element able to be used for mounting a spherical head onto a glenoid insert attachable on the glenoid cavity of the shoulder.

EP-A1-1.437.099 discloses a device for protecting and covering a femoral neck, which comprises a hollow sleeve able to be mounted on the reshaped femoral neck, and a rigid platelet or flange which extends outwards the sleeve and has a plurality of through holes for the passage of a relative fastener fixable to the bone.

However, these documents do not provide a solution for improving the attachment conditions of a prosthesis to a glenoid seating of a shoulder, more particularly for guaranteeing a correct and enduring attachment.

One purpose of the present invention is therefore to achieve a prosthesis of the shoulder, both of the anatomical or inverse type, suitable to guarantee an optimum attachment thereof to the scapula, substantially in any pathological and anatomical condition of the patient, or operating condition of the surgeon.

Another purpose of the present invention is to resolve the problems of the state of the art, in a simple and economical manner, without in any way affecting the correct functionality of the prosthesis.

Another purpose is to allow to modify, also over time, the conditions of attachment, for example as the consequence of a progressive bone degeneration, without intervening on the normal components of the prosthesis.

The Applicant has devised, tested and embodied the present invention to overcome the shortcomings of the state of the art and to obtain these and other purposes and advantages.

SUMMARY OF THE INVENTION

The present invention is set forth and characterized in the main claim, while the dependent claims describe other characteristics of the invention or variants to the main inventive idea.

In accordance with the above purposes, the invention provides to use an attachment element which is applied to an anatomical or inverse prosthesis of the shoulder for the articulation of a humerus in a scapula, of a shoulder having a glenoid cavity.

To be more exact, the attachment element is configured to be associated, when the prosthesis is assembled or pre-assembled, with the first articulation element associated with the top of the humerus, and/or with the second articulation element associated with the glenoid cavity.

According to a characteristic feature of the present invention, the attachment element comprises a first pin part for removably anchoring the attachment element to one and/or the other of the various components of the prosthesis, and at least a second winged part suitable to attach the prosthesis to the bone, or at least to improve the stability of its positioning on the bone, this second winged part being for example conformed as a fin.

In one preferred embodiment of the invention, the first pin part is an element of an inverse prosthesis configured to allow the mounting of a spherical head on a support associated to the top of said scapula, or an element of an anatomical prosthesis to allow the mounting of an articular insert on a support associated to the top of the scapula.

In another preferred embodiment, the first pin part has a conical shape, while in another preferred embodiment the first pin part has a double-conical shape, as disclosed for example in EP-A1-1.488.764.

The second winged part comprises one or more fins, each of which includes a first segment which extends substantially radially from the body of the first pin part and a second segment which is angled with respect to the first segment and is directed towards the bone upon which the prosthesis is to be fixed.

The second part, or winged part, is configured to protrude, when the attachment element of the prosthesis is in its assembled condition, with respect to the bulk determined by the prosthesis itself.

According to an embodiment of the invention, the second segment of each fin has at least a housing seating for attachment means, such as for example screws, pins, nails or other.

In one embodiment of the invention, each fin has the second segment substantially perpendicular to the first segment, i.e. the second segment is substantially parallel to the axis of the first pin part.

In another preferred embodiment, the fins are at least partly elastic so that their second segment may be applied with interference, with or without auxiliary screws or fasteners, onto the bone surface, in order to exert both a retaining effect of the prosthesis onto the bone and a containing action of the bone material itself.

Thanks to the disposition of the fin that protrudes from the normal bulk of the components of the prosthesis, the attachment means can be anchored on a bone part of the outer scapula and adjacent to the seating used to position the articulation elements of the prosthesis, for example the glenoid cavity.

The attachment element according to the invention therefore allows to guarantee, as an auxiliary or instead of the conventional screws that are anchored directly on the elements of the prosthesis, an optimum and enduring attachment of the prosthesis to the scapula, possibly modifiable over time.

This is because the presence of further attachment points with respect to those normally available in conventional prostheses, allows to attach the prosthesis in proximity with the glenoid cavity even in cases where the bone structure has particular pathologies, deformations and/or anatomies, or where the operating conditions of the surgeon are not optimum.

Moreover, the fin or fins can be positioned as desired around the periphery of the prosthesis, thus allowing to locate the positioning seating for the attachment means exactly in the position where the bone condition of the scapula requires.

There may be two or more fins, and each of them may have one, two or more housing seatings for attachment means, adjacent to each other longitudinally, laterally, diagonally or disposed reciprocally in another manner as desired.

The attachment element according to the present invention is very simple and economical, easy to position and assemble, and since it integrates perfectly with the other components of the prosthesis, it does not affect the correct functioning of the prosthesis.

Moreover, the attachment element can be selected as desired, on each occasion, and replaced, for example when a check-up is made, according to the specific conditions that are encountered and/or are determined also after the prosthesis has been assembled.

BRIEF DESCRIPTION OF THE DRAWINGS

These and other characteristics of the present invention will become apparent from the following description of some preferential forms of embodiment, given as a non-restrictive example with reference to the attached drawings wherein:

FIGS. 5a-5f show some constructional variants of the attachment element shown in FIG. 1.

DETAILED DESCRIPTION OF A
PREFERENTIAL FORM OF EMBODIMENT

Figure 1:
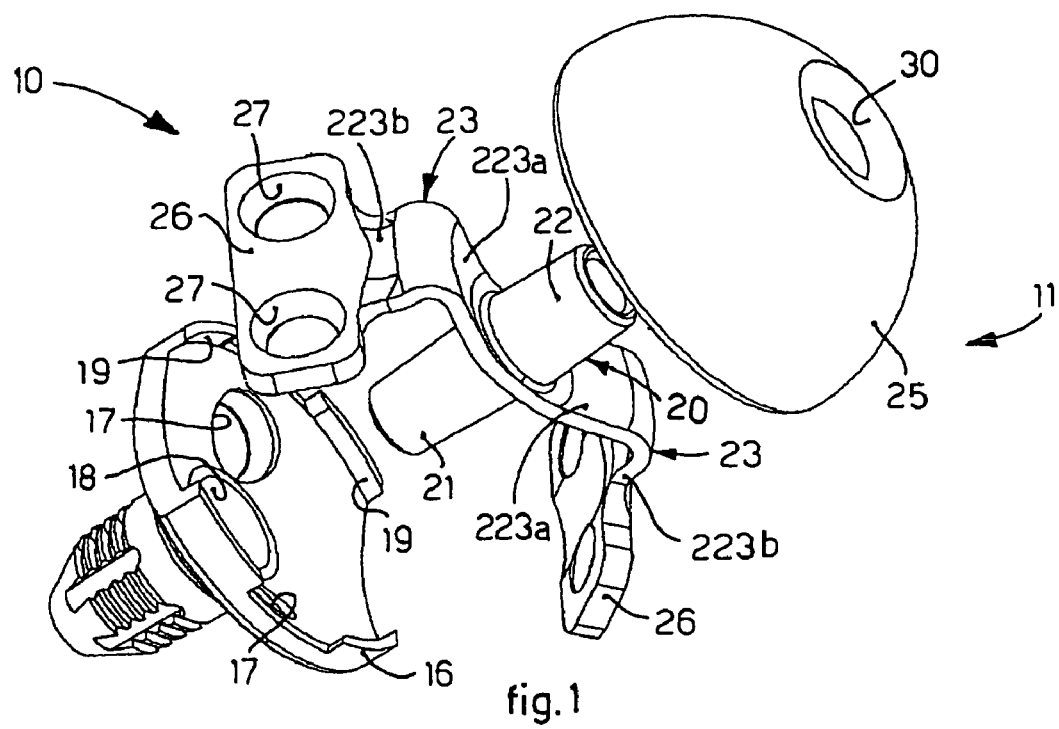
FIG. 1 is a three-dimensional exploded view of an attachment element according to the present invention applied to an inverse prosthesis of the shoulder.
Figure 2:
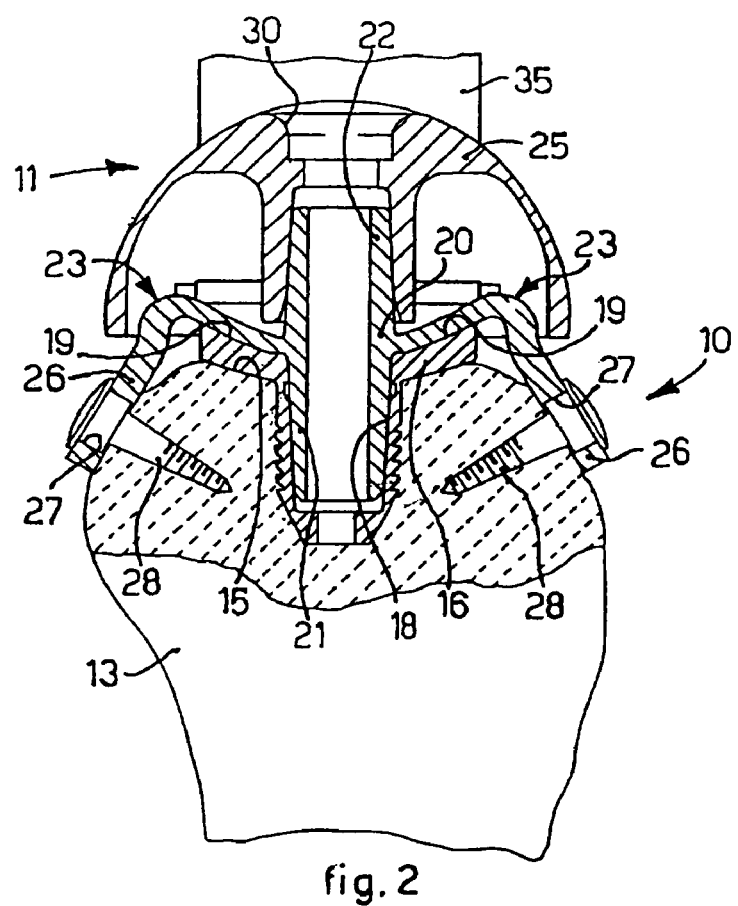
FIG. 2 is a longitudinal section of the prosthesis and the attachment element shown in FIG. 1, implanted in a glenoid cavity of a scapula.

With reference to FIGS. 1 and 2, an attachment element 10 according to the present invention is associated with an inverse prosthesis 11 implanted in a shoulder.

To be more exact, the inverse prosthesis 11 allows the articulation of a humerus, not shown, in a relative glenoid cavity 15 of a scapula 13, and comprises, on the side of the scapula 13, a metal support 16 inserted, for example by pressure, in a seating made in the glenoid cavity 15 and attached to the latter by means of central screws, not shown and of the traditional type, housed in corresponding holes 17.

The attachment element 10 according to the present invention comprises, in the solution shown here, a central metal pin 20 and lateral fins 23, in this case two, disposed radially at 180° with respect to the central pin 20.

Each lateral fin 23 comprises a first segment 223a which extends in a substantially radial direction from the central pin 20, and a second segment 223b which is angled, in this case substantially perpendicularly, with respect to the first segment 223a. The second segment 223b is directed towards the scapula 13 and is configured to attach on the bone lateral surfaces exerting on them a containing action. In an advantageous embodiment of the invention, the fin 23 is at least partly elastic, so that its second segment 223b may be attached on the bone of the scapula by interference, exerting a retaining action of the prosthesis, with or without auxiliary fixing elements, as disclosed in the following.

In the embodiments disclosed in the drawings, each lateral fin 23 is provided at one end with an attachment platelet 26 on which are made, in this case, two respective through holes 27 for housing lateral attachment screws 28. According to needs, there may be only one or three or more through holes 27 present on the attachment platelet 26.

It must be understood that the attachment element 10 can be chosen on each occasion according to the needs and the requirements deriving from the bone condition of the patient, i.e. with one or more fins 23, each fin 23 having one or more platelets 26, each platelet 26 having one or more holes 27 for screws 28 or other kind of fasteners.

The choice of the most suitable attachment element is not conditioned, or is conditioned only minimally, by the choice and geometry of the components of the prosthesis with which the attachment element 10 is associated because the same central pin 20 may be provided with the desired and/or needed number of fins 23, according to the conditions of the patient.

The support 16 of the inverse prosthesis 11 has an axial cavity 18 inside which a conical medial segment 21 of the central pin 20 of the attachment element 10 is inserted, so as to position the latter with its two lateral fins 23, or at least with the second segment 223b of them, protruding laterally from the bulk of the support 16 and of the prosthesis 11, thanks to the radial orientation of the first segment 223a of the fin 23 itself.

To be more exact, the two lateral fins 23 are positioned, with the first segment 223a thereof, in respective radial seatings 19 of the support 16, so as to be clamped angularly with respect to the latter.

Moreover, the second segments 223b of the two lateral fins 23 are bent towards the inside, i.e. towards the scapula 13, so that the through holes 27 are substantially facing respective lateral bone surfaces of the scapula 13, outside and adjacent with respect to the normal housing seatings of the prosthesis 11.

According to a variant solution, not shown, of the present invention, it is provided to attach the pin 20 to the support 16 by screwing, by bayonet means, by elastic interference, or other known methods.

The central pin 20 also has a lateral segment 22, opposite the medial segment 21 and also partly conical, on which a glenoid head 25, or glenosphere, made of metal material and with a hemispherical outer shape, is inserted.

It comes within the scope of the present invention to provide that, instead of being conical, the lateral segment 22 can consist of a screw or other suitable attachment system.

In the case shown here, the central pin 20 and the glenoid head 25 also have a longitudinal through hole suitable to accommodate an attachment screw, of a known type and not shown here, advantageously used as a safety element, in order to anchor the whole thus obtained to the glenoid cavity 15.

In this case, the glenoid head 25 has a hollow 30 on the outer surface, in which, during use, the head of the attachment screw is housed in retracted manner.

The inverse prosthesis 11 also comprises, on the side of the humerus, an attachment rod inserted into the humerus itself, which allows to attach and position, by means of a supporting body, a humeral cup 35, only partly shown in FIG. 2, made of metal material, and able to articulate with the convex surface of the glenoid head 25.

Figure 3:
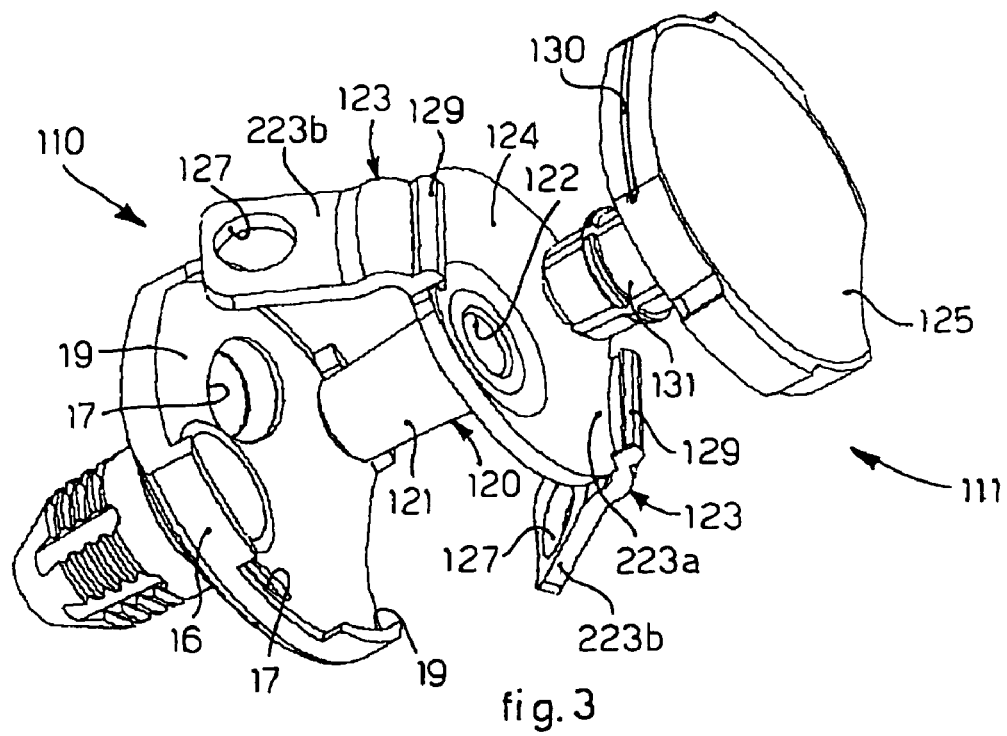
FIG. 3 is a three-dimensional exploded view of an attachment element according to the present invention applied to an anatomical prosthesis of the shoulder.
Figure 4:
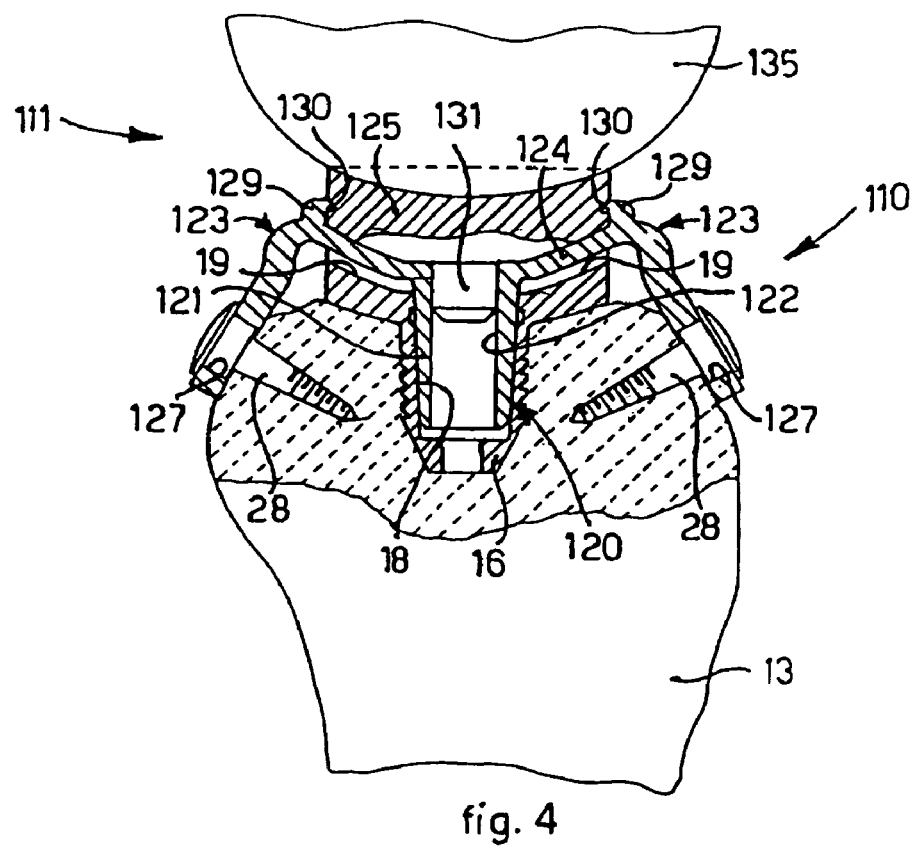
FIG. 4 is a longitudinal section of the prosthesis and the attachment element shown in FIG. 3, implanted in a glenoid cavity of a scapula.
Figure 5D:
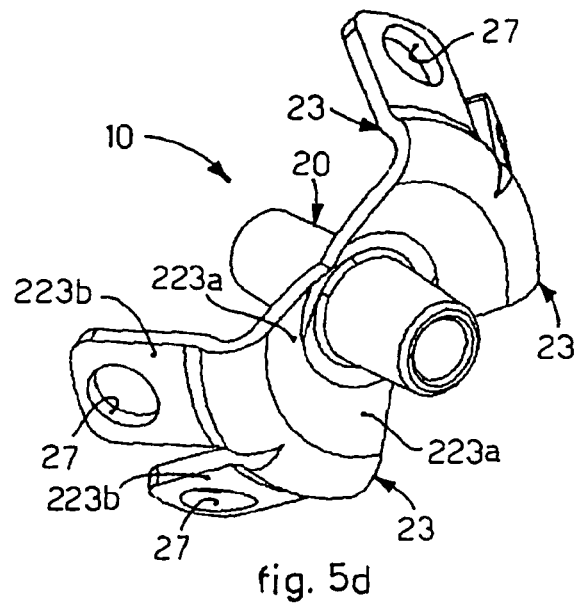
Figure 5E:
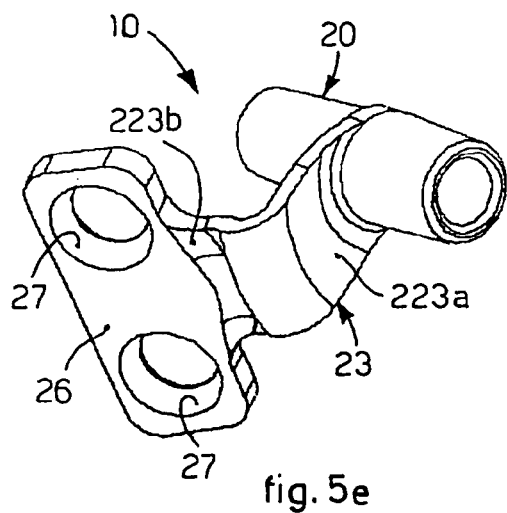
Figure 5F:
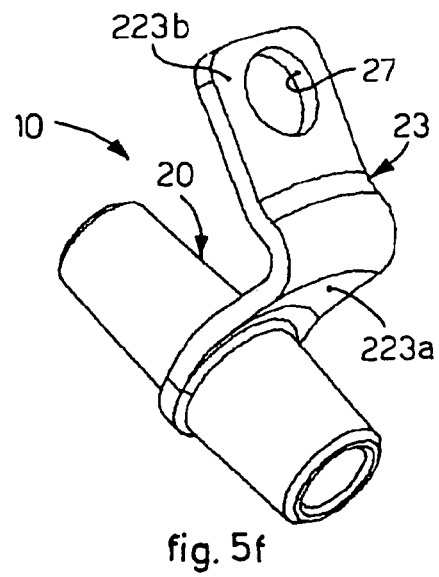

With reference to FIGS. 3 and 4, a constructional variant is shown of an attachment element 110 according to the present invention, in this case associated with an anatomical prosthesis 111 implanted in a shoulder.

To be more exact, the anatomical prosthesis 111 comprises, on the side of the scapula 13, a metal support 16, substantially equivalent to that of the inverse prosthesis 11, and inserted and attached in a traditional manner to the glenoid cavity 15 by means of central screws housed in the holes 17.

In this case, the attachment element 110 comprises a metal central pin 120, a supporting platelet 124 coaxial with the central pin 120, and two lateral fins 123 disposed radially at 180° with respect to the supporting platelet 124.

Each lateral fin 123 comprises a first segment 223a, which in this case is in one piece with said supporting platelet 124, substantially radial with respect to the pin 120, and a second segment 223b angled with respect to the first segment 223a and substantially parallel to the pin 120; the second segment 223b is provided at one end with a respective through hole 127 in order to house lateral attachment screws 28.

According to a variant, each lateral fin 123 is provided with two or more through holes 127.

The support 16 of the anatomical prosthesis 111 also has the two radial seatings 19 and an axial cavity 18 inside which a conical medial segment 121 of the central pin 120 of the additional attachment element 110 is inserted, so as to position the latter with its two lateral fins 123, or at least with the second segments 223b of them, protruding laterally from the bulk of the support 16 and the prosthesis 111.

To be more exact, in correspondence with the connecting segments between each lateral fin 123 and the supporting platelet 124, respective elastic hooks 129 are provided, able to cooperate with respective attachment seatings 130 made on the lateral surface of the glenoid cavity 15, so as to maintain the latter connected to the supporting platelet 124.

The two lateral fins 123 are also bent towards the inside in the part near the platelet 124, according to the angle defined between the first 223a and the second 223b segment of the fin 23, which is normally around 90°, so that the through holes 127 are substantially facing respective lateral bone surfaces of the scapula 13.

In this case, the central pin 120 also has an axial hole 122 inside which a positioning block 131 of an articular insert 125 is optionally inserted, made of plastic material, such as for example polyethylene.

The anatomical prosthesis 111 also comprises, on the side of the humerus, an attachment rod, not shown, inserted axially into the humerus, which allows to attach and position, by means of a supporting body, a humeral head 135, only partly shown in FIG. 4, made of plastic material, for example polyethylene or suchlike, and with a hemispherical outer shape, which articulates in the convex surface of the glenoid cup 125.

It is clear that modifications and/or additions of parts may be made to the additional attachment element 10 as described heretofore, without departing from the scope of the present invention.

According to some variant solutions of the present invention, as shown in FIGS. 5a to 5f, the attachment element 10, according to the different operating conditions, has:

- two fins 23, each having a first substantially radial segment 223a and a second substantially parallel segment 223b, with respect to a pin 20, which are angularly offset with respect to each other by 90° (FIG. 5a) where the through holes 27 are made directly at the ends of the second segment 223b of the fins 23;
- four lateral fins 23 offset with respect to each other by 90° (FIG. 5b) where the through holes 27 are made directly at the ends of the second segments 223b of the fins 23;
- two fins 23 angularly offset with respect to each other by 45° (FIG. 5c) where the through holes 27 are made directly at the ends of the second segments 223b of the fins 23;
- four fins 23 disposed in pairs and angularly offset two by two with respect to each other by 45° (FIG. 5d) where the through holes 27 are made directly at the ends of the second segments 223b of the fins 23;
- a single fin 23 (FIG. 5e), where the through holes 27 are made on an attachment bracket 26 disposed at the end of the second segment 223b of the fin 23;
- or a single fin 23 (FIG. 5f) where a single through hole 27 is made directly at the end of second segment 223b of the fin 23.

It also comes within the scope of the present invention to provide other constructional variants with respect to the possible variants mentioned above, just as the same variants can be provided also in the case where the additional attachment element 110 is of the type applicable to an anatomical prosthesis 111.

It is obvious that, if the additional attachment element 10, 110 is provided with a number of fins 23, 123 other than two, then the radial seatings 19 provided on the support 16 will also be made in a corresponding number ad angular position.

It is also clear that, although the present invention has been described with reference to some specific examples, a person of skill in the art shall certainly be able to achieve many other equivalent forms of additional attachment element for a prosthesis for the articulation of the shoulder, having the characteristics as set forth in the claims and hence all coming within the field of protection defined thereby.

The invention claimed is:

1. A prosthesis of the shoulder for the articulation of a humerus in a scapula of a shoulder having a glenoid cavity comprising an attachment element for said prosthesis, said prosthesis comprising at least a first articulation element associated with the top of said humerus, and a second articulation element associated with said glenoid cavity, the attachment element comprises:
- a first pin part for removable anchorage to said second articulation element associated with said glenoid cavity, and
- a second winged part for attachment of the prosthesis to the bone part of the scapula in a position outside the bulk of said first and second articulation element,
- said second winged part comprising a first segment which extends substantially radially from said first pin part, and a second segment which is angled with respect to said first segment and is directed towards the bone upon which said prosthesis is to be fixed,
- wherein said second winged part comprises at least a fin, said fin comprising said first and said second segment,
- wherein said second segment protrudes, when the attachment element is in its assembled condition, with respect to the bulk of the prosthesis, and
- A wherein said fin has a housing seating for auxiliary attachment means, and a support means is provided to attach the second articulation element to the glenoid cavity, said first pin part having at least a first conical segment able to be inserted into a respective cavity provided on the support means.

2. The prosthesis as in claim 1, wherein said fin is configured so that said housing seating, when the attachment element is in its assembled condition, is facing a bone part of said scapula, adjacent to the positioning seating of said articulation elements.

3. The prosthesis as in claim 1, wherein at least said second segment of said winged second part is at least partly elastic so as to be able to be attached to the lateral surface of said scapula by simple interference.

4. The prosthesis as in claim 1, wherein said second segment is substantially perpendicular to said first segment.

5. The prosthesis as in claim 1, wherein said first pin part has a second segment able to be inserted into a respective seating of said second articulation element.

6. The prosthesis as in claim 5, wherein said second segment of the first pin part is conical and cooperates with a mating conical seating of said second articulation element.

7. The prosthesis as in claim 5, wherein said second segment of the first pin part includes screw means or other system of attachment to said second articulation element.

8. The prosthesis as in claim 1, wherein said first pin part includes a hole in which a positioning element of said second articulation element is able to be inserted.

9. The prosthesis as in claim 1, wherein said second winged part comprises two fins disposed radially offset to each other with respect to said first pin part for removable anchorage.

10. The prosthesis as in claim 9, wherein said two fins are radially offset to each other substantially by 45° or multiples thereof, with respect to said first pin part for removable anchorage.

11. The prosthesis as in claim 1, wherein said second winged part comprises four fins disposed radially offset to each other with respect to said first pin part for removable anchorage.

12. The prosthesis as in claim 11, wherein said four fins are disposed radially offset to each other substantially by 45° to 90° with respect to said first pin part for removable anchorage.

13. The prosthesis as in claim 1, wherein each of said fins comprises two or more of said housing seatings for said attachment means.

14. The prosthesis as in claim 1, wherein said fin is provided at one end with a plate element on which said at least one housing seating is made.

15. The prosthesis as in claim 1, wherein said at least one fin is positioned, with said first segment, in a corresponding radial seating of a support plate, so as to be angularly clamped with respect to said support plate.

16. The prosthesis as in claim 1, wherein said at least one fin comprises, in said first segment, at least an elastic clamping element able to cooperate with respective attachment seatings made on the outer surface of said second articulation element, so as to keep it connected to said second articulation element.

17. The prosthesis as in claim 1, wherein said first pin part is an element of an inverse prosthesis configured to allow the mounting of a spherical head on a support associated to the top of said scapula.

18. The prosthesis as in claim 1, wherein said first pin part is an element of an anatomical prosthesis configured to allow the mounting of an articular insert on a support associated to the top of said scapula.

19. A prosthesis of the shoulder for the articulation of a humerus in a scapula of a shoulder having a glenoid cavity, comprising:
- a first articulation element associated with the top of said humerus, and
- a second articulation element associated with said glenoid cavity,
- a support comprising a hollow stem for inserting into the scapula and a radial seating,
- said hollow stem having a first end for embedding within the scapula away from the surface of the scapula and an second end opposed to the first end, said hollow stem having an outer surface for contacting the scapula
- said radial seating extending radially from the second end of the hollow stem;
- an attachment element comprising:
- a first pin part for inserting into the hollow stem of the support for removable anchorage to said second articulation element associated with said glenoid cavity, and
- a second winged part for attaching the prosthesis to the bone part of the scapula in a position outside the bulk of said first and second articulation element,
- said second winged part comprising a first segment for overlapping said radial seating of said support and which extends substantially radially from said first pin part, and a second segment which is angled with respect to said first segment and is directed towards the bone of the scapula upon which said prosthesis is to be fixed,
- wherein said second winged part comprises at least a fin, said fin comprising said first and said second segment,
- wherein said second segment protrudes, when the attachment element is in its assembled condition, with respect to the bulk of the prosthesis, and
- wherein said fin has a housing seating for auxiliary attachment means.

* * * * *